United States Patent [19]

Carlson et al.

[11] 4,220,860

[45] Sep. 2, 1980

[54] TOMOGRAPHIC SCANNER WITH CADMIUM TUNGSTATE SCINTILLATION CRYSTALS

[75] Inventors: Roland W. Carlson, Lyndhurst; Carl T. Jagatich, Chagrin Falls, both of Ohio

[73] Assignee: Ohio Nuclear, Inc., Solon, Ohio

[21] Appl. No.: 927,602

[22] Filed: Jul. 24, 1978

[51] Int. Cl.$^2$ .............................................. G01T 1/20
[52] U.S. Cl. .............................. 250/361 R; 250/368; 250/445 T
[58] Field of Search ............ 250/361 R, 363 R, 363 S, 250/366, 367, 369, 445 T, 483

[56] References Cited

U.S. PATENT DOCUMENTS

| | | | |
|---|---|---|---|
| 4,039,839 | 8/1977 | Carlier et al. | 250/483 |
| 4,068,129 | 1/1978 | Rabatin | 250/483 |
| 4,070,581 | 1/1978 | Gibbons et al. | 250/445 T |
| 4,114,042 | 9/1978 | LeMay | 250/445 T |
| 4,145,610 | 3/1979 | Perilhou | 250/445 T |

OTHER PUBLICATIONS

Scintillation Counters, Birks, McGraw-Hill, 1953, pp. 56-61, 121-125.
Luminescence and the Scintillation Counter, Curran, Butterworths Scientific Publications, London, pp. 82-89, 131-135.
Photoeffects in Silicon Surface—Barrier Diodes, Journal of Applied Physics, Luzzolino et al., vol. 33, No. 1, Jan. 1962, pp. 148-155.
Bismuth Germanate: A High-Z Gamma Ray and Charged Particle Detector, Harshaw Chemical Co., Solon, Ohio, pp. 1-6.
Harshaw Scintillation Phosphors, Harshaw Chemical Co., Solon, Ohio, 1975.
Harshaw Chemical Catalog, Other Harshaw Scintillation Phosphors, pp. 20-21, (date unknown).

Primary Examiner—Davis L. Willis
Attorney, Agent, or Firm—Fay & Sharpe

[57] ABSTRACT

A radiation detector suitable for use in tomographic scanners comprising at least one cadmium tungstate scintillation crystal optically coupled with a silicon photodiode or other photoelectric transducers. A plurality of cadmium tungstate crystals may be coupled to one silicon photodiode with fiber optic light guides. In a tomographic scanner, radiation passing through the scan circle impinges on the cadmium tungstate crystals causing them to scintillate. The light scintillated strikes the area of the p-n junction of the photodiode causing the photoelectric effect to be manifested. The intensity of radiation striking the crystal is determined by measuring the photoconductive conductance, photoemissive current or photovoltaic potential. From these intensities an image is computed of the radiation attenuation in the examined scan circle.

21 Claims, 4 Drawing Figures

TOMOGRAPHIC SCANNER WITH CADMIUM TUNGSTATE SCINTILLATION CRYSTALS

BACKGROUND OF THE INVENTION

This application pertains to the art of radiation detection apparatus and more particularly tomographic scanning apparatus. The invention is particularly applicable to rotating fan beam and traverse and rotate type tomographic scanners, and will be described with particular reference thereto. It will be appreciated, however, that the invention has broader applications such as X-ray or gamma ray counters and scintillation or nuclear cameras.

Tomographic scanners generally comprise a source of radiation, which subjects a region of a patient under examination to penetrating radiation such as x or γ radiation. Disposed opposite the patient from the source is one or more radiation detectors. The source of radiation is moved relative to the region of the patient under examination in order to subject it to radiation from a multiplicity of directions. In order to continue to detect the radiation passing through the patient as the source is moved, either (a) a plurality of detectors are positioned to be irradiated progressively or (b) the one or more radiation detectors are moved with the source.

Normally each detector means includes a scintillation crystal upon which radiation impinges. The radiation causes the scintillation crystal to luminesce with an intensity related to the intensity of the radiation. Optically connected with each crystal is a photoelectric transducer, most commonly a photomultiplier tube, for transforming the luminescence into electrical signals indicative of the intensity of radiation impinging upon the scintillation crystal. Usually an amplifier circuit is connected to each transducer for adjusting and calibrating the output of each transducer. This adjusted output signal may be related to the intensity of radiation or to the logarithm of the intensity. These output signals are processed with algorithms well-known in the computerized tomography art to produce a visual display of the examined region of the patient.

Although a number of crystalline substances are known to luminesce in the presence of radiation, bismuth germanium oxide ($Bi_4 Ge_3 O_{12}$, commonly referred to as BGO) is most often used in the radiation detectors of tomographic scanners. The reason other scintillators are not used varies. Some, such as thallium doped sodium iodide are hygroscopic—that is, as water is absorbed, the luminescent properties vary. Others such as cesium iodide and sodium iodide have a long decay constant or afterglow—that is, they continue to luminesce after the radiation is removed for a period of time that interferes with the reception of other signals. Still others luminesce with wave lengths incompatible with photoelectric transducers. Even BGO has draw backs. One of the principal problems with BGO scintillation crystals is a very low light conversion efficiency. For a given amount of radiation only a very small amount of luminescence is produced. Incident to the problem of low luminescent intensity is a variety of other problems. The low intensity requires the use of sensitive transducers—such as, photomultiplier tubes with their accompanying high voltage power supply. Furthermore, photomultiplier tubes are fairly large and, thus, result in physically large detector assemblies.

BGO's low luminescence intensity causes a relatively small variation in luminscence and a corresponding small variation in the output signal in reaction to variations in radiation intensity. The small amount of light BGO puts out is rapidly attenuated in fiber optic wave guides, thus restricting their use.

Yet another problem, suffered by tomographic scanners with BGO scintillation crystals, is the 480 nm characteristic wave length (blue light emission) of BGO luminescent light. This blue emission attenuates much more rapidly in fiber optic wave guides than does longer wave length light, such as yellow.

The low intensity levels of blue luminescence render BGO poorly compatible with silicon photodiodes, which produce a lower output than photomultiplier tubes and which are less sensitive to blue light.

SUMMARY OF THE INVENTION

The present invention contemplates a new and improved radiation detector which overcomes the above noted problems among others, and yet is simple and economical. In accordance with the present invention, there is provided a radiation detector which has a higher level of luminesce than BGO crystal, which is not hygroscopic and which luminesces with yellow light. In accordance with a more limited aspect of the invention, there is provided a radiation detector which has a cadmium tungstate scintillation crystal. Even more specifically, there is provided a radiation detector comprising an optically coupled cadmium tungstate scintillation crystal and a silicon photodiode. In one particular embodiment of the invention, a computerized tomographic scanner includes cadmium tungstate crystals for sensing radiation.

A major advantage of radiation detectors incorporating a cadmium tungstate crystal is that a much brighter luminescence from the same intensity of radiation is produced—about four times as great as BGO. This brighter luminescence provides a wider dynamic output range and allows a longer optical coupling distance between the crystal and the photoelectric transducer.

Another advantage occuring from the cadmium tungstate crystal is that the wave length of maximum emission is about 530 nm. This longer wave length in the yellow region provides better optical coupling with photodiodes, especially silicon photodiodes. Further, the longer wave length suffers less attenuation per unit length of fiber optic coupling.

Another advantage of the cadmium tungstate crystal radiation detector is that the afterglow is small.

BRIEF DESCRIPTION OF THE DRAWINGS

The invention may take physical form in certain parts and arrangement of parts, a preferred embodiment of which will be described in detail in the specification and illustrated in the accompanying drawings, which form a part thereof.

DESCRIPTION OF THE PREFERRED EMBODIMENT

Figure 1:
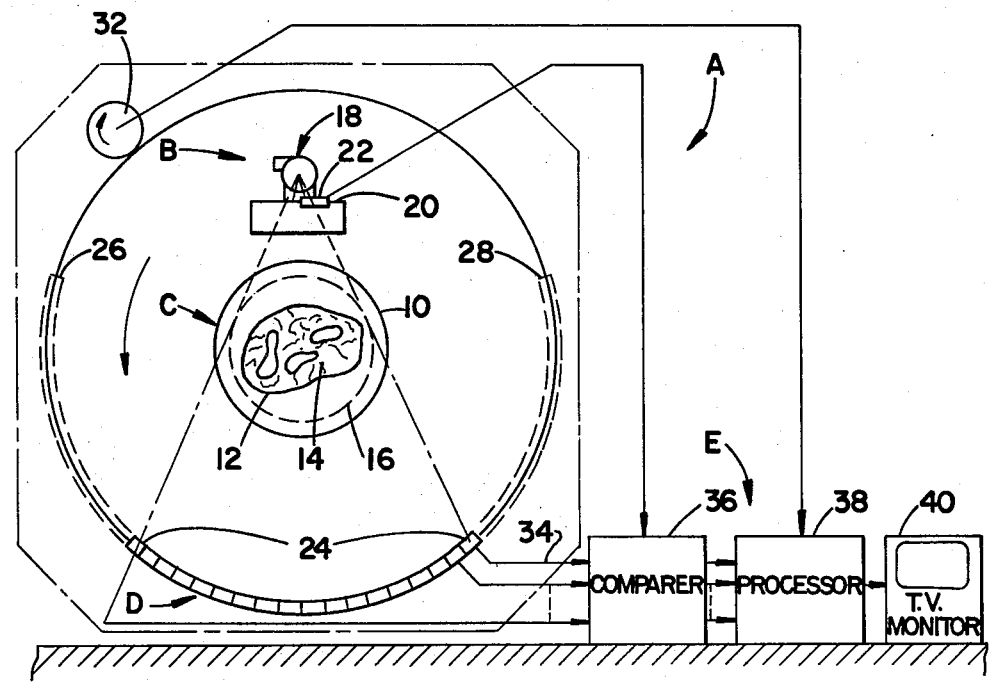
FIG. 1 shows a rotating fan beam tomographic scanner in accordance with the present invention.

Referring now to the drawings, which drawings are for the purposes of illustrating the preferred embodiment to the invention only and not for purposes of limiting the same. The figures show a tomographic scanner A, which includes a source of radiation B for subjecting a planar region of a patient C to penetrating radiation. Further, the scanner includes one or more radiation detectors D, the outputs of which are connected to a processing means E which implements algorithms well-known in the tomographic art to produce a visual image representation of the planar region of the patient examined.

Figure 2:
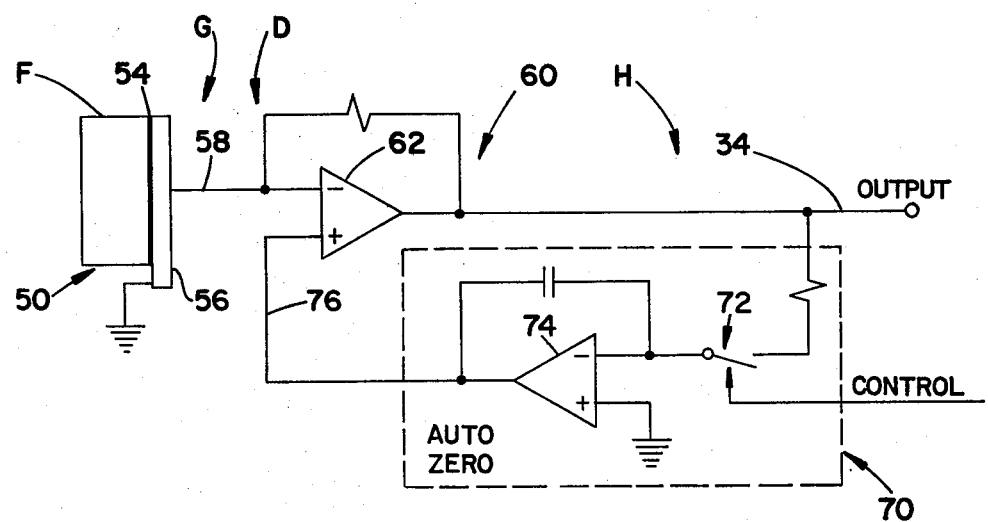
FIG. 2 shows a detail of a radiation detector in accordance with the present invention.

The radiation detectors D, shown in more detail in FIG. 2, include a cadmium tungstate scintillation crystal F which is optically coupled to a photoelectric transducer G. The radiation from source B which impinges upon crystal F will cause the crystal to luminesce or give off light with an intensity related to the intensity of radiation impinging thereon. As the intensity of light from crystal F impinging upon transducer G varies, physical properties of transducer G change. If G is a photodiode with a photosensitive p-n junction, then in accord with the phenomenon known as the photo effect, various properties of the p-n junction will change.

The photoelectric effect is an interaction between radiation and matter resulting in the absorption of photons and the consequent liberation of electrons. Covered by this term are three separate phenomena, in which a measurable electric effect is influenced by incident radiation: the photoconductive effect, the photoemissive effect and the photovoltaic effect.

The photoconductive effect is manifested as a change in the electric conductance of the solid or liquid, in which the charge carriers are not in thermal equilibrium with the lattice. Many semiconducting metals and their compounds evidence a marked increase in electrical conductance when electromagnetic radiation (e.g. light) is incident on them.

The photoemissive effect occurs in many semiconducting materials and their compounds. In such materials incident radiation, such as light, causes the emission of electrons from the lattice. The emitted electrons can be marshalled into a current flow, which current flow varies in strength with the intensity of incident radiation.

The photovoltaic effect is evidenced by a no load potential between layers of layered arrangements of certain semiconducting materials with conducting or other semiconducting materials in the presence of incident radiation, such as light. Incident radiation causes a migration of electrons between the lattices of the layered materials resulting in an excess of electrons in one lattice and a deficit in another. This causes a no load potential difference between layers, which potential difference varies with the intensity of incident radiation.

Any of these light controlled properties may be monitored to produce a signal indicative of the intensity of the liminescence, hence, the intensity of radiation impinging upon the scintillation crystal. However, photodiode manufacturers generally recommend measuring the photoemissive current, where small, varying intensities are to be measured.

The output from the photoelectric transducer is modified and amplified by a circuit H, which calibrates the output so that a given intensity of radiation will produce a given output signal.

FIG. 1 illustrates a rotating fan beam tomographic scanner in accordance with the present invention. A patient position defining means 10 in the form of a cylinder provides a support for a patient or part of the patient 12, which is to be examined. A planar region 14 of the patient to be examined is positioned toward the center of cylinder 10 so that a scan circle 16 circumscribes the region of interest.

The source of radiation B for subjecting the region of the patient under examination to radiation includes a X-ray tube 18 although gamma rays or other forms of penetrating radiation may be used. A collimator and shutter combination 20 selects the size of the scan circle 16, which the beam of radiation will span and blocks the beam of radiation between scans. Further, a reference detector 22 may be mounted adjacent to the collimator 20 for monitoring the intensity of radiation at the source B.

The radiation detectors D are elements of a radiation detection means which includes arc of detectors 24, which arc at least encompasses the detectors upon which the fan beam of radiation impinges. The radiation detectors are so positioned opposite the patient C from radiation source B that as the source moves, the radiation passing through the patient may be utilized. This, of course, may be done either by moving the arc of detectors 24 in conjunction with the source or by positioning a sufficiently large number of detectors around the patient. If a stationary arc is used, it may extend from 180° to 360°. A particular embodiment is illustrated in phantom in FIG. 1 in which the detectors D are located in the arc between detectors 26 and 28 which spans 180° plus the angle of the fan beam.

Relative motion between the source of radiation B and the patient is caused by means for moving 32 the radiation source. In the fan beam embodiment, this moving means rotates at least the source of radiation B about the patient position defining means 10.

The individual detectors D produce output signals on electrical lines 34, which are indicative of the intensity of radiation impinging thereon. The output lines 34 are connected with processing means E. Included in the processing means is a comparator 36 which monitors the intensity of radiation received by reference detector 22, and adjusts the signals on output lines 34 thereby. One way of making this adjustment is by subtracting the logarithm of the intensity received at reference detector 22 from the logarithm of the radiation intensity at each of the radiation detectors D.

Comparator 36 is connected with a processor 38, which may either be a device such as disclosed in copending application Ser. No. 838,084 or be a digital computer programmed to implement the algorithms set forth in the article "Reconstruction for Divergent Ray Data", A. V. Lakshminarayanan, Tech. Report No. 92, State University of New York at Buffalo (1975). The processor is connected with video monitor 40 upon which a representation of the radiation attenuation in the planar region of the patient examined is displayed.

FIG. 2 shows one of the radiation detectors D which, of course, may also be used in other radiation detecting apparatus. The detectors described in FIG. 2 may be used both as a reference detector 22 and as radiation detectors D in the arc of detectors 24.

Shown in FIG. 2 is a means 50 for sensing incident radiation. This means includes scintillation crystal F optically coupled to photoelectric transducer G. Scintillation crystal F is a cadmium tungstate ($CdWO_4$) crystal. In the preferred embodiment, the cadmium tungstate crystal is grown from starting material which is 0.999999 pure (99.9999%). Impurities in the crystal increase the amount of thermoluminescence which lengthens the decay constant. Because time intervals between sampling of the scintillation crystal by processing means E are short, it is desirable that the crystal have a short decay constant. A long decay constant such as caused by a large amount of thermoluminescence prohibits the total luminescence from varying rapidly and accurately with variations in the incident radiation. High thermoluminescence degrades the data by, in effect, carrying over luminescence from previous radiation samplings into subsequent samplings of the detector. Thus although cadmium tungstate of other purities may be used, there is a trade off between purity and thermo-luminescence although other purities of starting material may be workable.

Cadmium tungstate is ideally suited for tomographic scanners—it has a wave length of maximum emission at 530 nm, is not hydroscopic, and is approximately four times as efficient as BGO in converting incident radiation energy to light.

Scintillation crystal F is optically coupled with a conventional optical cement 54 to photoelectric transducer G. In the preferred embodiment, the photoelectric transducer is photodiode 56 such as a gallium arsenide or doped silicon p-n junction photodiode.

As discussed above the current, voltage and conductive properties of photodiode 56 vary with intensity of light impinging upon the junction. Further as indicated above, any one of these varying properties may be monitored at the photodiode output 58 of the photodiode 56. The photocurrent property is the preferred property to be measured. The output 58 is connected to amplification and calibration means H.

Calibration amplifier circuit means H includes an amplifier means 60, which transforms the current signal on one input on line 58 into a voltage signal with magnitude corresponding to the intensity of radiation impinging upon the scintillation crystal. Amplifier means 60, including a low noise FET operational amplifier 62, transforms the current analog signal into a voltage analog signal on output line 34. Alternately, a current analog signal may be produced on line 34.

Circuit means H also includes an automatic zero means 70. The automatic zero means automatically calibrates the output signal on line 34 so that the voltage is proportional to the intensity of radiation impinging upon the scintillation crystal. The automatic zero means includes a switch 72, which is caused to be closed at a time when there is no radiation impinging upon scintillation crystal F. Switch 72 may be controlled by processor 38. Any output voltage, when the crystal is dark, is fed to one input of an operational amplifier 74 which produces an offset voltage on a line 76 operatively connected to another input of amplifier 62. The automatic zero means adjusts the offset voltage on line 76 until the voltage on line 34 is zero.

When switch 72 is opened, the automatic zero means continues to apply the same offset voltage on line 76. Thus, the output signal on line 34 has the operation amplifier offset voltage removed and is directly indicative of radiation intensity.

Figure 3:
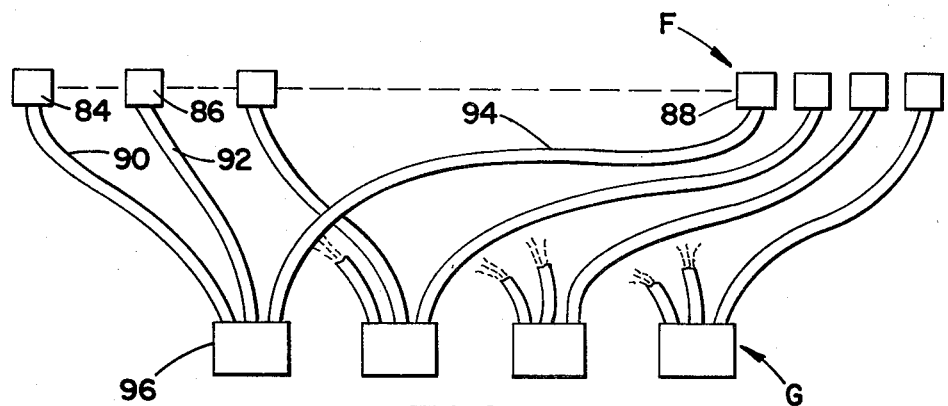
FIG. 3 shows an alternate embodiment of the optical coupling between scintillation crystals and photoelectric transducers in accordance with the present invention.

FIG. 3 shows an alternate embodiment in which a fiber optic system is used for optically coupling scintillation crystals to the photoelectric transducers. It will be noticed in FIG. 1 that if an entire ring of radiation detectors are used only a fraction of them will be irradiated at any given time. In that arrangement, the number of transducers can be reduced by coupling a plurality of scintillation crystals to a single photoelectric transducer. The coupled crystals are spaced in such a manner that no two are irradiated at any one time. For example, three scintillation crystals 84, 86, and 88 are coupled respectively with fiber optic light guides or light pipes 90, 92, and 94 to transducer 96. This transducer may be either a photodiode as discussed above or a photomultiplier tube. In fact less sensitive and less expensive PM tubes may be used with the $CdWO_4$ because of its greater output. A suitable photomultiplier tube has found to be Hamamatsu side view photomultiplier tube Model No. R-300. The yellow light from the cadmium tungstate scintillation crystals is attentuated to a lesser degree than blue light from a BGO scintillation crystal would be in traversing the light pipe. Thus, longer fiber optic light guides may be utilized without any significant degradation of the resulting signal. In some applications it may be desirable to have a single scintillation crystal connected to a plurality of photoelectric transducers. This can be accomplished analogously to FIG. 3 by attaching or optically coupling one end each of a plurality of light pipes to one or more faces of a single scintillation crystal and to one or more photoelectric transducers at the other end.

Figure 4:
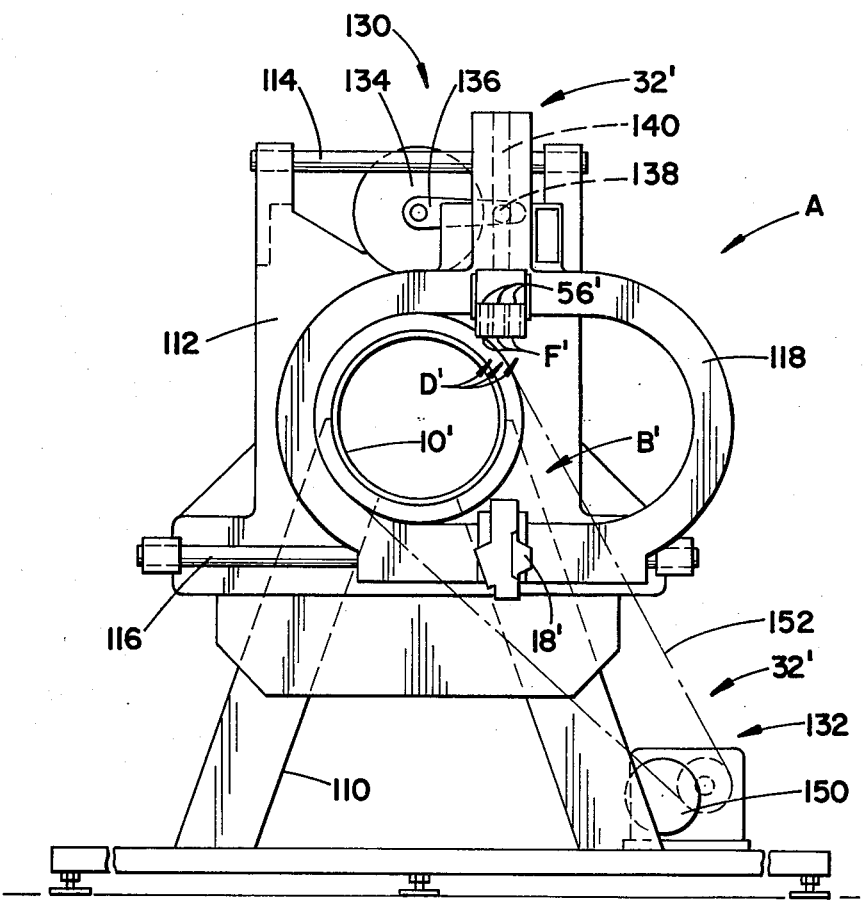
FIG. 4 shows an alternate embodiment of a traverse and rotate tomographic scanner in accordance with the present invention.

FIG. 4 illustrates another alternate embodiment of the tomographic scanner incorporating the present invention. The tomographic scanner A', of FIG. 4 is of the type commonly known as traverse and rotate type scanner. It includes a source of radiation B' producing one or more finger beams of radiation, which strike a corresponding number of radiation detection means D'. The source of radiation and the radiation detectors are movable linearly across and rotatably about the means 10' for defining a patient position. In operation, the source and detectors traverse across the patient position are rotated a few degrees and again traverse patient position. This traverse and rotate procedure is repeated until a multiplicity of data sets representing the radiation attenuation along said parallel paths through the planar region of the patient from different directions are gathered. Such machines have been sold commercially by Ohio-Nuclear, Inc. of Solon, Ohio.

A support 110 holds cylinder 10' for supporting the patient. Rotatably mounted about cylinder 10' is a frame 112, which carries a pair of parallel bars 114 and 116. Slidably mounted on bars 114 and 116 is a carriage 118 for carrying the source of radiation B' and the radiation detectors D'.

The source of radiation B' includes a radiation or X-ray tube 18' mounted in a housing which has a collimator for defining three finger beams of radiation. Radiation detection means includes three radiation detectors D'. Each radiation detector has a cadmium tungstate scintillation crystal F' and a photoelectric transducer 56' such as a silicon photodiode.

The means 32' for moving the radiation source relative to the patient position includes a traverse drive means 130 and a rotational drive means 132. The traverse drive means includes a motor 134 with a lever arm 136 attached to its armature shaft. The lever arm is attached to a follower 138 which rides in a vertical track 140 on carriage 118. As the motor rotates, lever arm 136 engages track 140 with follower 138 and causes the carriage to slide back and forth along the parallel bars 114 and 116.

Between each traverse, a rotational drive means 132 rotates the frame 112 a few degrees. The rotational drive means includes a motor means 150 for causing a chain drive 152 to rotate the frame 112 incrementally.

A processing means, not shown, but analogous to FIG. 1 is connected with each of the detectors D'. The processing means as used herein includes all hardware and software necessary to process received radiation and may include a programmable digital computer programmed to implement the algorithms set forth in the article "Fourier Reconstruction of the Head Section", L. A. Shepp and B. F. Logan, IEEE Transactions and Nuclear Science, June, 1974, or "Optimal Reconstruction of a Function from its Projections" Logan and Shepp, Duke Mathematics Journal, Vol. 42, No. 4, Dec., 1975. Such processing means are available in machines commercially available from Ohio Nuclear, Inc. and others.

Invention has been described with reference to the preferred embodiment. Obviously modifications and alterations will occur to others upon reading and understanding of this specification. Although the radiation detection detector is ideally suited for use of tomographic scanners, other uses and applications thereof are readily apparent. It is our intention to include all such modifications and alterations insofar as they come within the scope of the claims or the equivalence thereof.

We claim:

1. A tomographic scanner for examining a planar region of a patient comprising a scan circle defining an examined region; a source of radiation moveably mounted relative to said scan circle for subjecting the scan circle to radiation; radiation detection means positioned to receive at least some of the radiation that has passed from said source and through the scan circle for producing signals indicative of the intensity of radiation impinging thereon; processing means operatively connected with said detection means for transforming said signals into a visual display caused by radiation attenuation in the scan circle;

said radiation detection means comprising at least one cadmium tungstate scintillation crystal optically connected with at least one photoelectric transducer.

2. The tomographic scanner as set forth in claim 1 wherein said cadmium tungstate scintillation crystal is 0.999999 pure.

3. The tomographic scanner as set forth in claim 1 wherein said photoelectric transducer is a photodiode.

4. The tomographic scanner as set forth in claim 3 wherein said photodiode is a silicon photodiode.

5. The tomographic scanner as set forth in claim 3 further including an amplifier means having an input operatively connected with said photodiode and an output on which is produced the signal indicating the intensity of radiation impinging on the scintillation crystal.

6. The tomographic scanner as set forth in claim 5 wherein said amplifier means is an operational amplifier and further including an automatic zero means having an input controllably connected to said output, and an automatic zero output connected to an input of said operational amplifier for providing an offset voltage to said operational amplifier which offset voltage is related to said intensity indicating signal when the crystal is receiving no radiation whereby the automatic zero means removes from the output signal an operation amplifier offset voltage component so that the output signal is directly related to the intensity of radiation received by the scintillation crystal.

7. The tomographic scanner as set forth in claim 1 wherein said scintillation crystal is optically connected to said photodiode by means of a fiber optic light guide.

8. The tomographic scanner as set forth in claim 7 wherein a plurality of scintillation crystals are optically connected to said photodiode.

9. The tomographic scanner as set forth in claim 1 further including a reference detector positioned to receive radiation not passing through the patient for monitoring the intensity of the source of radiation, said reference detector comprising a cadmium tungstate scintillation crystal optically connected with a photodiode.

10. In a radiographic diagnostic apparatus which irradiates a subject with x or gamma radiation, produces electrical signals corresponding to the intensity of some radiation which has traversed the subject, and produces a diagnostic indication from the electrical signals, the improvement comprising a wide dynamic range radiation detector comprising:

(a) a scintillation crystal of crystalline cadmium tungstate disposed to receive at least some of the radiation which has traversed the subject; and, (b) a solid state photoelectric transducer optically connected with said scintillation crystal whereby said transducer produces the electrical signal corresponding to the intensity of radiation received by the scintillation crystal.

11. The radiographic diagnostic apparatus as set forth in claim 10 wherein said photoelectric transducer is a gallium arsenide photodiode.

12. The radiographic diagnostic apparatus as set forth in claim 10 further including fiber optic light guide means optically connecting said scintillation crystal and said transducer.

13. The radiographic diagnostic apparatus as set forth in claim 12 further including an additional scintillation crystal, said fiber optic light guide means optically connecting said additional scintillation crystal to said transducer whereby the transducer is responsive to light from both scintillation crystals.

14. The radiographic diagnostic apparatus as set forth in claim 10 wherein said transducer is a photodiode.

15. The radiographic diagnostic apparatus as set forth in claim 12 wherein said photodiode is sensitive to light in the yellow range.

16. The radiographic diagnostic apparatus as set forth in claim 14 further including an amplifier means having an input operatively connected with said photodiode and an output on which is produced an output signal representing the intensity of radiation received by said scintillation crystal.

17. The radiographic diagnostic apparatus as set forth in claim 16 wherein said amplifier means is an operational amplifier and further including an automatic zero means having an input controllably connected to said output, and an automatic zero output connected to an input of said operational amplifier for providing an offset voltage to said operational amplifier which offset voltage is related to said output signal when the crystal is receiving no radiation whereby the automatic zero means removes from the output signal an operational amplifier offset voltage signal component so that the output signal is directly related to the intensity of radiation received by the scintillation crystal.

18. The radiographic diagnostic apparatus as set forth in claim 16 wherein the input to said amplifier means detects a current from said photodiode, which current has a magnitude indicative of the intensity of radiation received by said scintillation crystal, and wherein said amplifier means transforms the photodiode current into an output voltage, which is proportional to the intensity of radiation received by said scintillation crystal.

19. The radiographic diagnostic apparatus as set forth in claim 16 wherein said output signal is a current, which is proportional to the intensity of radiation received by said scintillation crystal.

20. The radiographic diagnostic apparatus of claim 14 wherein said photodiode produces a photoemissive current indicative of the intensity.

21. In a tomographic scanner for examining a region of a patient with radiation, the scanner comprising:
a means for defining a patient position;
a source of radiation for subjecting said patient position to radiation, radiation detection means for receiving at least part of said radiation;
said detection means including means for sensing radiation;
the improvement comprising at least one $CdWO_4$ scintillation crystal included in the means for sensing radiation.

* * * * *